(12) United States Patent
Horppu et al.

(10) Patent No.: US 8,491,607 B1
(45) Date of Patent: Jul. 23, 2013

(54) ELASTIC SURGICAL RING CLIP/LOADER AND A METHOD

(75) Inventors: Petri Horppu, Gothenburg (SE); Birger Amrén, Onsala (SE); Gudmund Dvärsäter, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/380,519

(22) PCT Filed: Jul. 12, 1999

(86) PCT No.: PCT/SE99/01259
§ 371 (c)(1),
(2), (4) Date: Sep. 3, 1999

(87) PCT Pub. No.: WO00/03642
PCT Pub. Date: Jan. 27, 2000

(30) Foreign Application Priority Data

Jul. 15, 1998 (SE) ........................................ 9802553
May 31, 1999 (SE) ........................................ 9901998

(51) Int. Cl.
*A61B 17/10* (2006.01)
(52) U.S. Cl.
USPC ........................................................ 606/140
(58) Field of Classification Search
USPC .................. 606/140, 108, 139, 141, 151, 153, 606/155; 128/830, 842, 843; 411/35, 46–48
See application file for complete search history.

(56) References Cited

U.S. PATENT DOCUMENTS

| | | | | |
|---|---|---|---|---|
| 3,911,923 | A | * | 10/1975 | Yoon .............................. 606/141 |
| 4,493,319 | A | * | 1/1985 | Polk et al. ..................... 606/141 |
| 4,548,201 | A | * | 10/1985 | Yoon .............................. 606/141 |
| 4,794,927 | A | * | 1/1989 | Yoon .............................. 606/140 |
| 4,840,523 | A | * | 6/1989 | Oshida ............................ 411/48 |
| 4,860,746 | A | * | 8/1989 | Yoon .............................. 128/830 |
| 5,122,149 | A | | 6/1992 | Broome |
| 5,632,581 | A | * | 5/1997 | Hasada ........................... 411/48 |
| 5,643,290 | A | * | 7/1997 | Clark et al. ................... 606/141 |
| 5,843,121 | A | * | 12/1998 | Yoon .............................. 606/206 |

FOREIGN PATENT DOCUMENTS

| | | |
|---|---|---|
| DE | 92 05 453.6 | 7/1992 |
| JP | 11158943 | 6/1989 |

* cited by examiner

*Primary Examiner* — Thomas McEvoy
(74) *Attorney, Agent, or Firm* — White & Case LLP

(57) ABSTRACT

Mounting apparatus for mounting an endless cord (2) which is expandable from a contracted condition to an expanded condition onto an end (1) of a structure having a transverse dimension greater than that of the cord when in the contracted condition comprising a tapered adaptor (14; 114) for the cord to be propelled over onto the end of the structure having a forward smaller end (16; to 116) for location in the cord in its contracted condition and a rear larger end (18; 118) for juxtaposing with the end of the structure and an expander device (24; 124; 224) movable relative to the adaptor to propel the cord over the adaptor onto the rear larger end thereof.

9 Claims, 6 Drawing Sheets

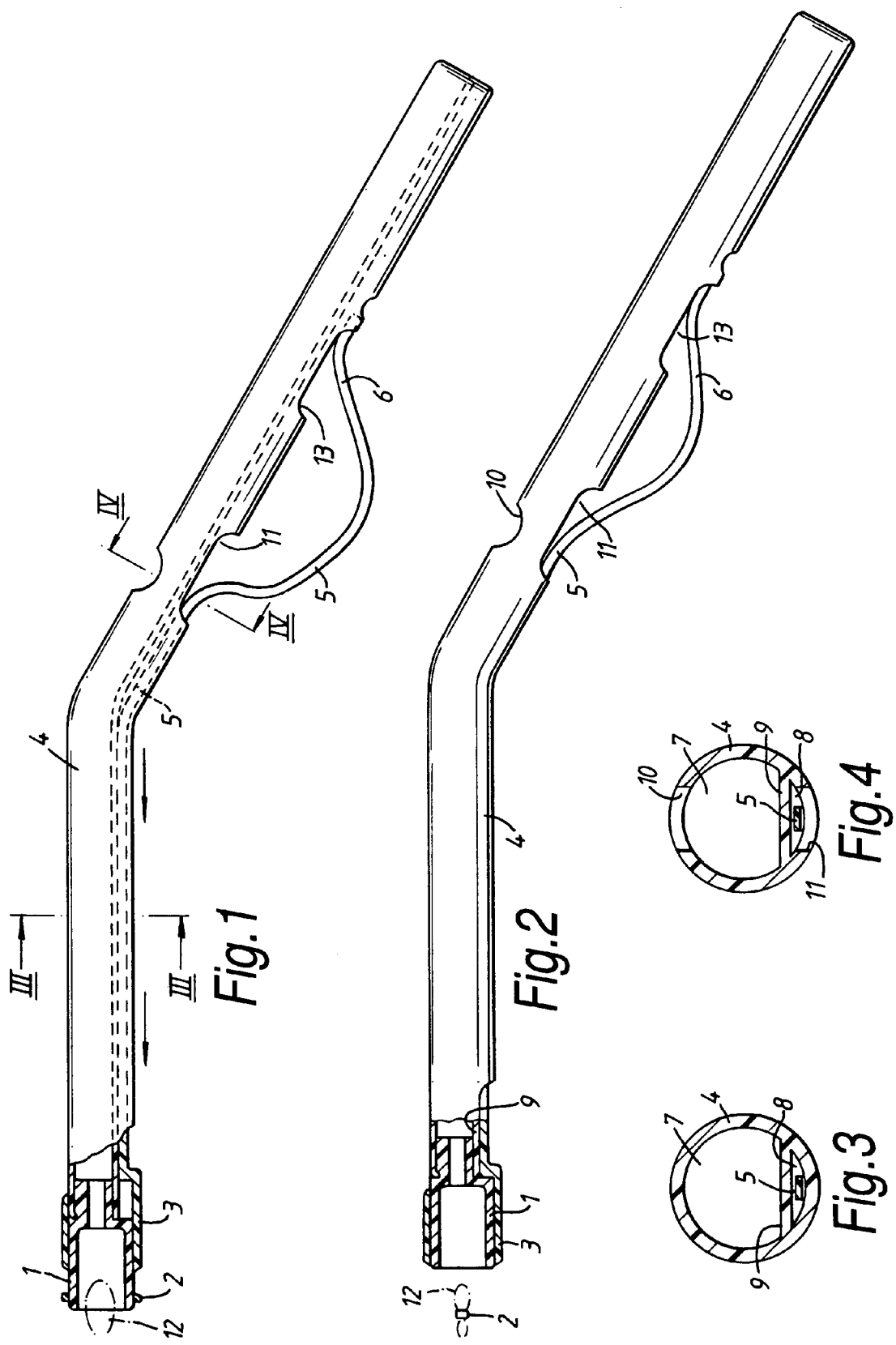

Figure 5:
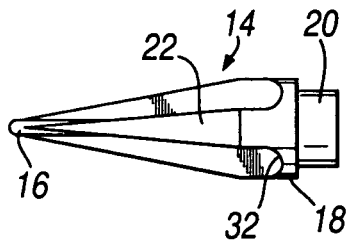

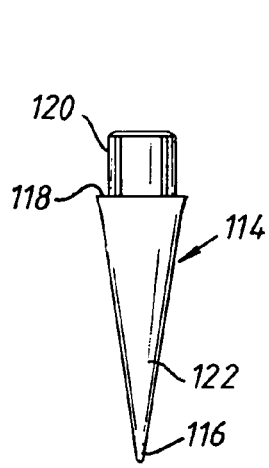
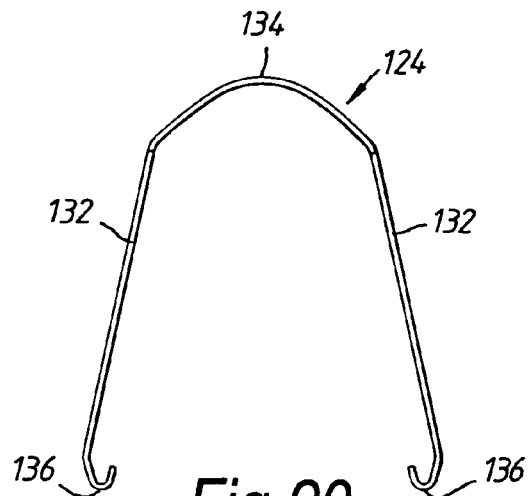
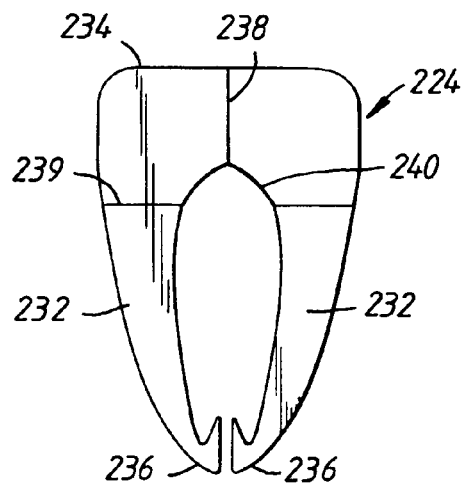
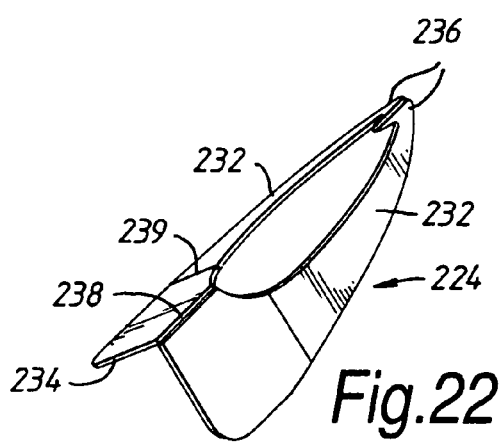
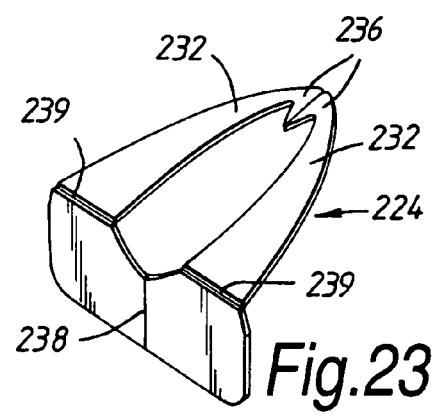

ELASTIC SURGICAL RING CLIP/LOADER AND A METHOD

FIELD OF THE INVENTION

The present invention relates to a mounting apparatus for mounting an expandable endless cord or band such as an elastic cord or O-ring on an end of a structure which has a transverse dimension greater than that of the cord when in a contracted condition. The invention is particularly, although not exclusively, concerned with a mounting apparatus for mounting an elastic endless cord or band on a surgical instrument for ligating internal tissues of a cavity in the human body by means of the elastic cord or band, one example being the ligation of haemorrhoids.

BACKGROUND OF THE INVENTION

A surgical instrument for ligating haemorrhoids is disclosed in European patent EP 0310582 B1, the contents of which are incorporated herein by reference. This surgical instrument, which will be referred to herein as a "surgical instrument of the type defined", includes an inner front cylinder with the elastic cord stretched around its front end and an outer discharge cylinder displaceably arranged on the inner front cylinder to push the elastic cord off the inner front cylinder to close around the stem of a haemorrhoid when inserted in the inner front cylinder.

In its normal rest or contracted condition the generally circular elastic cord is of considerably smaller diameter than the external diameter of the inner front cylinder. The elastic cord is mounted on the inner front cylinder by means of a conical adaptor of circular cross-section having a larger rear end which makes a push fit in the inner front cylinder. The adaptor is tapered forwardly to its pointed front end which fits into the elastic cord when in its rest condition. The cord is then pushed or rolled by hand along the adaptor on to the inner front cylinder by the user, usually the surgeon. Difficulties arise because the elastic cord is small and the user has to wear gloves as protection against infection. This is especially true when the user has to perform several consecutive ligations.

It is an aim of the invention to alleviate the above-mentioned difficulties.

SUMMARY OF THE INVENTION

According to a first aspect of the invention there is provided a mounting apparatus for mounting an endless cord which is expandable from a contracted condition to an expanded condition onto an end of a structure having a transverse dimension greater than that of the cord when in the contracted condition, the apparatus comprising a tapered adaptor for the cord to be propelled over onto the end of the structure having a forward smaller end for location in the cord in its contracted condition and a rear larger end for juxtaposing with the end of the structure and an expander device movable relative to the adaptor to propel the cord over the adaptor onto the rear larger end thereof.

In an embodiment of the invention such as hereinafter to be described the rear larger end of the adaptor is an axial section of the adaptor.

In an embodiment of the invention such as hereinafter to be described the end of the structure and the rear larger end of the adaptor each have a generally circular outer surface profile.

In an embodiment of the invention such as hereinafter to be described the adaptor and the expander device are adapted to mesh with one another to propel the cord over the adaptor to the rear larger end thereof.

In an embodiment of the invention such as hereinafter to be described the adaptor comprises a plurality of circumferentially spaced-apart fingers which extend from the rear larger end towards the forward smaller end and the expander device comprises a plurality of circumferentially spaced-apart arms insertable between the fingers of the adaptor. Preferably, the fingers and arms are equi-spaced on the adaptor and expander device.

In an embodiment of the invention such as hereinafter to be described the forward smaller end of the adaptor is presented by a central member. Where the adaptor has circumferentially spaced-apart fingers, the fingers and central member may be connected to one another.

The adaptor of the mounting apparatus of the invention may be made from a plastics material such as polypropylene, for instance by injection moulding. Where the adaptor has the central member, however, the central member may be made from metal instead.

In an embodiment of the invention such as hereinafter to be described the expander device is operable in a first mode to propel the cord over the adaptor onto the rear larger end thereof and in a second mode to propel the cord from the rear larger end onto the end of the structure. To this end, the expander device may comprise a tubular section adapted to slide over the adaptor to propel the cord from the rear larger end onto the end of the structure.

In another embodiment of the invention such as hereinafter to be described the expander device is operable in a single mode to propel the cord over the adaptor onto the end of the structure.

In an embodiment of the invention such as hereinafter to be described the expander device takes the form of a hook device which comprises two opposed hooks dimensioned to engage the cord when in its contracted condition, the hook device being adapted for the hooks to engage with the cord when in its contracted condition and to be displaced away from one another when the hook device is moved relative to the adaptor to propel the cord over the adaptor to the rear larger end thereof.

In an embodiment of the invention such as hereinafter to be described the hooks are located at the ends of opposed arms made of a resilient material such as metal wire, preferably spring metal wire.

In an embodiment of the invention such as hereinafter to be described the hook device includes a crease for enabling the hooks to be brought close together for engagement with the cord when in its contracted condition. The hook device may include a further crease for enabling the adaptor to be moved into position adjacent the hooks.

As with the adaptor, the expander device may be made from a plastics material such as polypropylene, for instance by injection moulding.

The mounting apparatus of the invention is particularly, although not exclusively, suited for mounting an elastic cord onto an end of a surgical instrument for ligating internal body tissue, for example the inner front cylinder of a surgical instrument of the type defined.

According to a second aspect of the invention there is provided a surgical kit comprising a mounting apparatus according to the first aspect of the invention. The surgical kit may further comprise a surgical instrument for ligating internal body tissue, for example a surgical instrument of the type defined.

According to a third aspect of the invention there is provided a method of mounting an endless cord which is expandable from a contracted condition to an expanded condition onto an end of a structure having a transverse dimension greater than that of the cord in its contracted condition comprising the steps of providing a tapered adapter having a forward smaller end and a rear larger end, propelling the cord over the tapered adaptor onto the rear larger end thereof by displacement of an expander device relative to the adaptor and, when the rear larger end of the tapered adaptor is juxtaposed to the end of the structure, propelling the cord from the rear larger end of the adaptor onto the end of the structure.

In an embodiment of the invention according to its third aspect such as hereinafter to be described displacing the expander device relative to the adaptor propels the cord over the adaptor onto the end of the structure. As an example, this may be achieved by using an expander device in the form of a hook device which comprises two hooks dimensioned to engage with the cord when in its contracted condition, engaging the hooks with the cord when the cord is in its contracted condition, displacing the hook device relative to the adaptor so as to propel the cord over the adaptor onto the end of the structure and disengaging the hooks from the cord.

Exemplary embodiments of the invention will now be described with reference to the accompanying Figures of drawings.

BRIEF DESCRIPTION OF THE ACCOMPANYING FIGURES OF DRAWINGS

Figure 6:
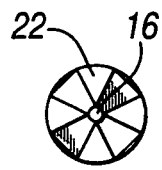
Figure 7:
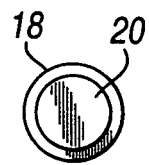
Figure 8:
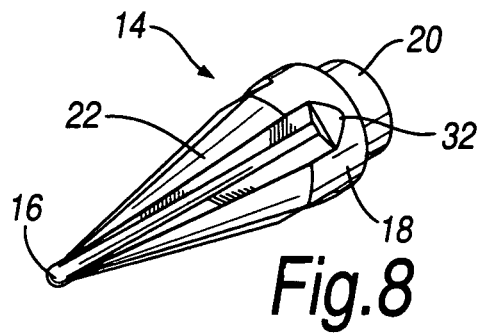
Figure 9:
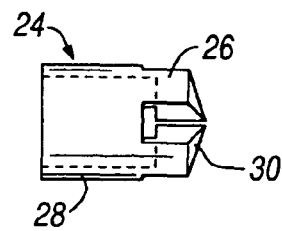
Figure 11:
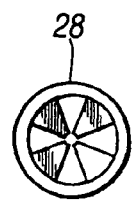
Figure 10:
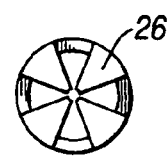
Figure 12:
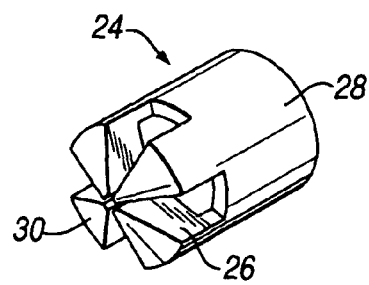
Figure 13:
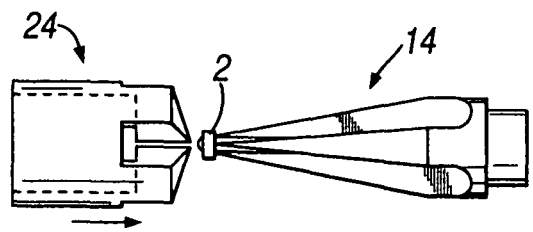
Figure 14:
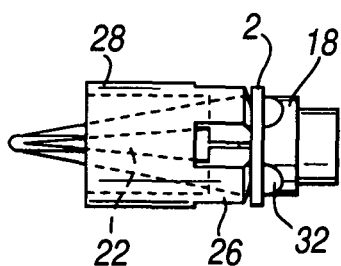
Figure 15:
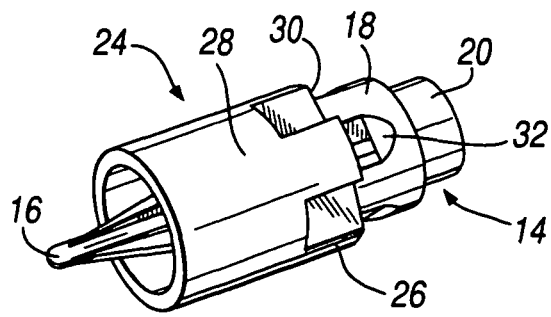
Figure 16:
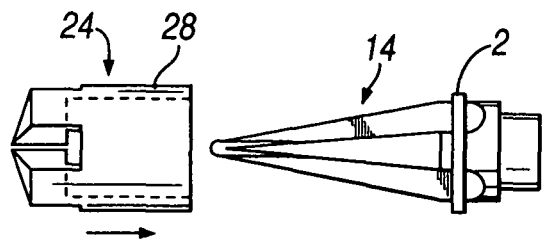
Figure 17:
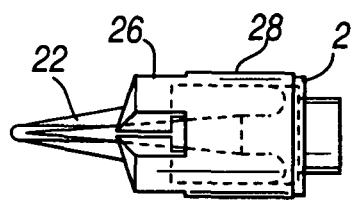
Figure 18:
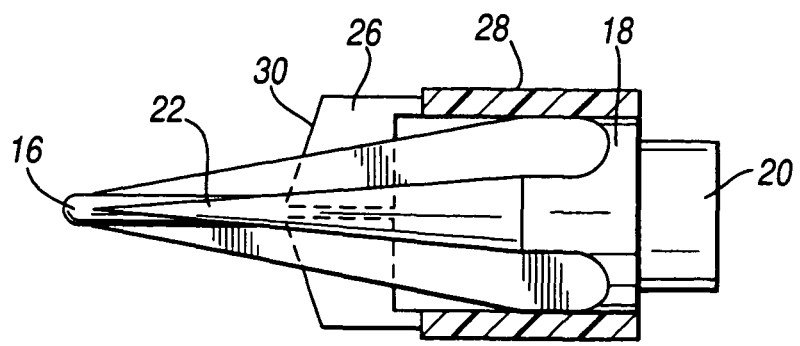

FIG. 1 is a side elevation, partly in section, of a surgical instrument of the type defined in a rest position, FIG. 2 is side elevation, partly in section, of the surgical instrument of FIG. 1 in an actuated position, FIG. 3 is an enlarged sectional view along the line in FIG. 1, FIG. 4 is an enlarged sectional view along the line IV-IV in FIG. 1, FIG. 5 is a side elevation of an adaptor of a mounting apparatus according to a first embodiment of the invention, FIG. 6 is a front view of the adaptor of FIG. 5, FIG. 7 is a rear view of the adaptor of FIG. 5, FIG. 8 is a perspective view of the adaptor of FIG. 5, FIG. 9 is a side elevation of an expander device of the mounting apparatus according to the first embodiment of the invention, FIG. 10 is a front view of the expander device of FIG. 9, FIG. 11 is a rear view of the expander device of FIG. 9, FIG. 12 is a perspective view of the expander device of FIG. 9, FIG. 13 is a side elevation of the adaptor of FIG. 5 supporting an elastic cord and the expander device of FIG. 9 in a first mode of operation for propelling the cord along the adaptor, FIG. 14 is a side elevation corresponding to FIG. 13 with the expander device in its first mode of operation located on the adaptor and the elastic cord having been propelled by the expander device onto a rear cylindrical section of the adaptor, FIG. 15 is a perspective view of the expander device of FIG. 9 in its first mode of operation located on the adaptor of FIG. 5, FIG. 16 is a side elevation of the adaptor of FIG. 5 with the cord supported on the rear cylindrical section thereof and the expander device of FIG. 9 in a second mode of operation for pushing the cord off the rear cylindrical section, FIG. 17 is a side elevation corresponding to FIG. 16 with the expander device in its second mode of operation located on the adaptor and the elastic cord having been pushed to the rear edge of the rear cylindrical section of the adaptor, FIG. 18 is a side elevation of the expander device of FIG. 9 (in cross-section) in its second mode of operation located on the adaptor of FIG. 5 with the elastic cord having been pushed off the rear cylindrical section of the adaptor, FIG. 19 is a side elevation of an adaptor of a mounting apparatus according to a second embodiment of the invention, FIG. 20 is a side elevation of an expander device of the mounting apparatus according to the second embodiment of the invention which is in the form of a first hook device, FIG. 21 is a side elevation of another expander device of the mounting apparatus according to the second embodiment of the invention which is in the form of a second hook device, FIG. 22 is a perspective view of the second hook device when folded along a first crease, and FIG. 23 is a perspective view of the second hook device when folded along a second crease.

DETAILED DESCRIPTION OF THE EXEMPLARY EMBODIMENTS

In FIGS. 1 to 4 there is shown a surgical instrument for the ligation of haemorrhoids in a patient having an angled tube (4) which is connected at its front end to an inner front cylinder (1) having an inner volume dimensioned to receive a located haemorrhoid (12).

As shown in FIGS. 3 and 4, the angled tube (4) is divided longitudinally by a partition wall (9) into a first part (7) and a second part (8). The first part (7) of the tube is adapted to be connected to a vacuum source at its rear end. A restriction hole (10) is situated in the upper side of the tube (4) in a position that is convenient to reach by an operator's finger or thumb when the operator's hand grips a rear part of the angled tube (4). The size of the hole (10) is such that it is capable of being covered by the finger or thumb of the operator.

FIG. 1 shows the surgical instrument in a rest position in which an outer discharge cylinder (3) is displaceably mounted on the inner front cylinder (1) in a rearward rest position relative to the inner front cylinder (1) and an elastic cord (2) is stretched around the front part of the inner front cylinder (1). The discharge cylinder (3) is connected to one end of a strip (5) which extends rearwardly in the second part (8) of the tube from the outer discharge cylinder (3) to the rear part of the tube (4) where it is secured, passing out of a forward guiding hole (11) positioned in the lower side of the rear part of the angled tube (4) and back into the tube (4) through a rear guiding hole (13) longitudinally spaced from the forward guiding hole (11) to form an actuating loop (6) outside of the tube (4) the purpose of which will become clear hereinafter.

In operation, the rear end of the first part (7) of the tube (4) is connected to a vacuum source and the forward part of the tube (4) is inserted into the anal cavity of the patient's body. The restriction hole (10) is covered by the operator's finger or thumb to create a vacuum in the inner front cylinder (1) whereby the located haemorrhoid (12) is sucked into the inner front cylinder (1). By means of the fingers of the operator's hand, the actuating loop (6) is pressed towards the tube (4) causing the strip (5) to push the outer discharge cylinder (3) forwardly on the inner front cylinder (1). As shown in FIG. 2, the forward movement of the outer discharge cylinder (3) on the inner front cylinder (1) pushes the elastic cord (2) off the inner front cylinder (1) onto the base of the haemorrhoid (12) to shut off the blood circulation thereto.

The restriction hole (10) is then opened to counterbalance the vacuum in the inner front cylinder (1) whereupon the instrument is removed from the anal cavity of the patient and the discharge cylinder (3) displaced back to its rearward rest position by the strip (5) ready for another elastic cord (2) to be mounted on the front part of the inner front cylinder (1). To this end, a mounting apparatus in accordance with the present invention is provided for mounting the elastic cord (2) on the front part of the inner front cylinder (1) of the surgical instrument so that a further ligation can be carried out.

There will now be described with reference to FIGS. 5 to 18 a mounting apparatus according to a first embodiment of the invention. Referring first to FIGS. 5 to 8, the mounting apparatus according to the first embodiment includes an adaptor (14) which is attachable to the inner front cylinder (1). The adaptor (14) has a central rod (16) extending forwardly along the axis of a cylindrical body (18). The rear end of the rod (16) is connected to the cylindrical body (18) and the forward end of the rod (16) is sufficiently small to enter the elastic cord (2) when in its rest or contracted condition. A mounting plug (20) extends rearwardly from the cylindrical body (18) and is dimensioned so as to make a push fit in the inner front cylinder (1) of the surgical instrument in order to mount the adaptor on the inner front cylinder (1). When mounted on the inner front cylinder (1), the outer surface of the cylindrical body (18) of the adaptor (14) is flush with or slightly larger in diameter than the outer surface of the inner front cylinder (1). Four equispaced fingers (22) are mounted at their rear ends to the circumference of the cylindrical body (18) and converge towards the central rod (16) such that the forward ends of the fingers (22) rest on the central rod (16) immediately behind the forward extremity thereof.

The adaptor (14) may be made of any suitable plastics material such as polyvinyl chloride or the thermoplastic material polypropylene, for example by injection moulding. Alternatively, the central rod (16) may be made of any suitable metal with the rest of the adaptor (14) being formed from a plastics material.

As shown in FIGS. 9 to 12, the mounting apparatus according to the first embodiment further comprises an expander device (24) having four equi-spaced arms (26) mounted at their rear ends to the circumference of the forward end of a tube (28). The arms (26) converge from the circumference of the tube (28) so that their forward ends (30) are spaced apart at a distance equal to or slightly greater than the diameter of the central rod (16) of the adaptor (14). The tube (28) is dimensioned so as to make an easy sliding fit on the cylindrical body (18) of the adaptor (14).

The expander device (24) may be made of any suitable plastics material such as polyvinyl chloride or the thermoplastic material polypropylene, for example by injection moulding.

In operation of the mounting apparatus according to the first embodiment, the adaptor (14) is attached to the inner front cylinder (1) of the surgical instrument and the elastic cord (2) placed on the tip of the central rod (16) as previously described. As will be understood by reference to FIGS. 13 to 15, the expander device (24) is manoeuvred to locate the forward ends (30) of the arms (26) of the expander device (24) around the central rod (16) of the adaptor (14) in the spaces between the fingers (22). The expander device (24) is then pushed into the adaptor (14) so that the arms (26) and fingers (22) mesh with one another thereby causing the arms (26) to push the elastic cord (2) along the fingers (22) and onto the forward part of the cylindrical body (18) of the adaptor (14). As shown in FIG. 14, when the elastic cord (2) has reached this position the forward ends (30) of the arms (26) come into contact with a front face (32) of the cylindrical body (18) thereby preventing further movement of the arms (26) into the adaptor (14).

As will be understood by reference to FIGS. 16 to 18, the expander device (24) is then withdrawn from the adaptor (14), turned around and the tube (28) slid over the cylindrical body (18) of the adaptor (14) to push the elastic cord (2) from the cylindrical body (18) onto the inner front cylinder (1) of the surgical instrument. The adaptor (14) and expander device (24) are then removed from the inner front cylinder (1) leaving the surgical instrument ready for ligating another haemorrhoid.

It is envisaged that the adaptor (14) and the expander device (24) may be designed so that the above-mentioned first movement of the expander device (24) onto the adaptor (14) will locate the elastic cord (2) on the inner front cylinder (1) of the surgical instrument thus avoiding the need to withdraw and reverse the expander device (24) onto the adaptor (14).

The expander device (24) may be provided with a surface structure which gives good purchase of the expander device (24). As non-limiting examples, there may be mentioned texturing or roughening of the surface or the provision of an annular flange on the surface.

In FIGS. 19 to 23 there is shown a mounting apparatus according to a second embodiment of the invention. As shown in FIG. 19, the mounting apparatus according to the second embodiment includes an adaptor (114) having a forward tapered portion (122) and a rearward mounting plug (120) dimensioned to make a push fit in the inner front cylinder (1). The tapered portion (122) has a pointed front end (116) which is sufficiently small to enter the elastic cord (2) when in its rest condition and a rear end (118) which is dimensioned to be flush with or slightly larger than the outer surface of the inner front cylinder (1) when the adaptor (114) is secured thereto. The adaptor (114) is made of any suitable plastics material such as polyvinyl chloride or the thermoplastic material polypropylene.

Referring to FIG. 20, the mounting apparatus according to the second embodiment further comprises a first hook device (124) made of resilient wire and having two opposed arms (132) which are joined by a bowed connecting portion (134). At the end of each arm (132) a hook (136) is provided. The hooks (136) are sufficiently small that they can both enter the elastic cord (2) when in its rest condition, and these hooks (136) are blunted to avoid tearing the surgeon's gloves and clothing or damaging the elastic cord (2).

When the first hook device (124) is in its rest position the arms (132) are spaced apart as illustrated in FIG. 20. In operation of the mounting apparatus of the second embodiment, the arms (132) are initially pressed towards one another to enable the hooks (136) to be hooked through the elastic cord (2) and then released to enable the resilience of the connecting portion (134) to move the hooks (136) apart to expand the elastic cord (2) sufficiently to be mounted on the forward tip (116) of the adaptor (114) which has been, or will be, secured to the inner front cylinder (1). The first hook device (124) is then moved rearwardly with respect to the adaptor (114). The rearward movement of the first hook device (124) relative to the adaptor (114) causes the arms (132) to be progressively expanded outwardly back towards their rest position whereby the hooks (136) and hence the elastic cord (2) are concomitantly expanded outwardly. As a result, the cord (2) is drawn over the adaptor (114) onto the forward part of the inner front cylinder (1) by the first hook device (124). The hooks (136) are then removed from the stretched cord (2) and the adaptor (114) removed from the inner front cylinder (1) leaving the instrument ready-for-use.

Referring to FIGS. 21 to 23, in place of the first hook device (124) there may be used a second hook device (224) made through injection moulding of a plastics material such as for example polypropylene. The second hook device (224) has two arms (232) joined by a connecting portion (234) with a hook (236) being formed at the end of each arm (232).

A first crease or hinge line (238) extends longitudinally along the centre of the connecting portion (234) and a second crease or hinge line (239) extends laterally across the rear of the two arms (232).

Folding the second hook device (224) along its first crease (238) brings together the two arms (232) and hooks (236) to enable the hooks (236) to be hooked into the elastic cord (2) when in its rest condition. The first crease (238) is then opened out to cause the arms (232) and the hooks (236) to move apart and thereby stretch the elastic cord (2). The second hook device (224) is then folded or hinged along its second crease (239) to enable the adaptor (114) to pass over a recessed part (240) of the connecting portion (234) as the second hook device (224) is moved rearwardly with respect to the adaptor (114) to pull the elastic cord (2) over the adaptor (114) and onto the inner front cylinder (1). As the second hook device (224) is moved rearwardly with respect to the adaptor (114) the arms (232) move outwardly to expand the elastic cord (2) progressively as it is pulled over the adaptor (114) and onto the inner front cylinder (1). After the elastic cord (2) is placed on the inner front cylinder (1) the hooks (236) are released from the elastic cord (2) leaving the instrument ready-for-use.

Guide tracks may be provided to extend longitudinally along the adaptor (114) to guide the hooks (136; 236) of the first and second hook devices (124; 224) when mounting the elastic cord (2) on the inner front cylinder (1). Such tracks may be diametrically opposed on the adaptor (114).

The mounting apparatus described hereinabove with reference to the accompanying Figures of drawings reduces the problems encountered when an operator of the surgical instrument has to manipulate the elastic cord with a gloved hand.

It will be understood that the present invention has been described in relation to exemplary embodiments and can be modified in many different ways within the scope of the invention as defined by the appended claims. Finally, it should be noted that the reference numerals in the appended claims are solely for guidance and not to be construed as having a limiting effect on the claims.

The invention claimed is:

1. A mounting apparatus for mounting an endless cord which is expandable from a contracted condition to an expanded condition onto an end of a structure having a transverse dimension greater than that of the cord when in the contracted condition, said apparatus comprising a tapered adaptor for the cord to be completely propelled over onto the end of the structure, wherein the adaptor comprises a forward smaller end for location in the cord in its contracted condition, a rear larger end for juxtaposing with the end of the structure and a plurality of circumferentially spaced-apart fingers extending from the rear larger end towards the forward smaller end, and wherein the adaptor is provided with a mounting plug extending rearwardly from the rear larger end for mounting the adaptor to the structure and having an outer diameter that is smaller than the outer diameter of the rear larger end, and said apparatus further comprising an expander device movable relative to the adaptor to propel the cord over the adaptor onto the rear larger end thereof and completely onto the end of the structure, wherein the expander device has an outer circumference and comprises a plurality of circumferentially spaced-apart arms insertable between the fingers of the adaptor, and wherein the thickness of each arm tapers continuously from the outer circumference in a radial direction towards the center of the circumference.

2. The mounting apparatus as claimed in claim 1, wherein the expander device is operable in a first mode thereof to propel the cord over the adaptor on to the rear larger end thereof and in a second mode thereof to propel the cord from the rear larger end onto the end of the structure.

3. The mounting apparatus as claimed in claim 2, wherein the expander device includes a tubular section adapted to slide over the adaptor to propel the cord from the rear larger end thereof onto the end of the structure.

4. The mounting apparatus as claimed in claim 1, wherein the adaptor and the expander device are adapted to mesh with one another to propel the cord over the adaptor to the rear larger end thereof.

5. The mounting apparatus as claimed in claim 1, wherein the thickness of the circumferentially spaced-apart fingers of the adaptor taper in a longitudinal direction towards the forward smaller end of the adaptor.

6. The mounting apparatus as claimed in claim 1, wherein the adapter comprises a central member presented at the forward smaller end of the adaptor.

7. The mounting apparatus as claimed in claim 6, wherein the central member and the fingers of the adaptor are connected to one another.

8. A surgical kit comprising a mounting apparatus as claimed in any one of claim 1, 2 or 4-3.

9. The surgical kit as claimed in claim 8, further comprising a surgical instrument for ligating internal body tissue.

* * * * *

UNITED STATES PATENT AND TRADEMARK OFFICE
CERTIFICATE OF CORRECTION

PATENT NO.        : 8,491,607 B1
APPLICATION NO.   : 09/380519
DATED             : July 23, 2013
INVENTOR(S)       : Petri Horppu et al.

Page 1 of 1

It is certified that error appears in the above-identified patent and that said Letters Patent is hereby corrected as shown below:

In the Claims

In claim 8, column 8, line 45, "claim 1, 2 or 4-3" should read --claims 1-7--.

Signed and Sealed this
Twenty-ninth Day of October, 2013

Teresa Stanek Rea
*Deputy Director of the United States Patent and Trademark Office*